United States Patent [19]

Tomioka et al.

[11] 4,097,664
[45] *Jun. 27, 1978

[54] DERIVATIVES OF AN ANTIBIOTIC XK-62-2

[75] Inventors: Shinji Tomioka, Machida; Yasuki Mori, Kawasaki, both of Japan

[73] Assignee: Abbott Laboratories, North Chicago, Ill.

[*] Notice: The portion of the term of this patent subsequent to Feb. 28, 1995, has been disclaimed.

[21] Appl. No.: 704,750

[22] Filed: Jul. 12, 1976

[30] Foreign Application Priority Data

Jul. 15, 1975 Japan .................................. 50-85767
Jul. 15, 1975 Japan .................................. 50-85768

[51] Int. Cl.² ............................................. C07H 15/22
[52] U.S. Cl. ........................................ 536/17; 424/180
[58] Field of Search ........................................... 536/17

[56] References Cited

U.S. PATENT DOCUMENTS

| 3,725,385 | 4/1973 | Freiberg | 536/17 |
| 3,796,698 | 3/1974 | Naito et al. | 536/17 |
| 3,796,699 | 3/1974 | Naito et al. | 536/17 |

Primary Examiner—Johnnie R. Brown
Attorney, Agent, or Firm—Fitzpatrick, Cella, Harper & Scinto

[57] ABSTRACT

New 3''-N-demethyl- and 3''-N, 6'-N-didemethyl-1-α-hydroxy-ω-aminoacyl derivatives of the antibiotic XK-62-2, their pharmaceutically-acceptable acid addition salts, and a process for preparing the same are disclosed.

8 Claims, 2 Drawing Figures

DERIVATIVES OF AN ANTIBIOTIC XK-62-2

BACKGROUND OF THE INVENTION

1. Field of the Invention

The present invention relates to new derivatives of the antibiotic XK-62-2, their acid addition salts, and a process for preparing the same.

2. Description of the Prior Art

XK-62-2, a known antibiotic described in copending U.S. patent application Ser. No. 364,058, filed May 25, 1973, represented by the formula:

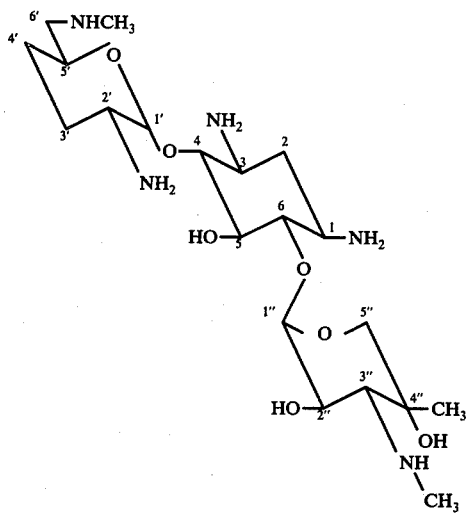

Antibiotic XK-62-2 and processes for producing the same are also set forth in Okachi et al, The Journal of Antibiotics, Vol. XXVII, No. 10, pages 793–800, 1974.

Briefly stated, as disclosed in the aforementioned U.S. Patent Application Ser. No. 364,058 (the disclosure of which is hereby expressly incorporated herein by reference), antibiotic XK-62-2 is readily produced by culturing actinomycetes such as *Micromonospora sagamiensis*. More specifically, strains of the above-mentioned microorganisms such as *Micromonospora sagamiensis* ATCC 21826, ATCC 21827, ATCC 21803 and ATCC 21949 are inoculated into a liquid medium containing a carbon source which the microorganism can utilize such as sugars, hydrocarbons, alcohols, organic acids, etc.; inorganic or organic nitrogen sources and inorganic salts and growth promoting factors and are cultured at 25°–40° C for 2 to 12 days until substantial anti bacterial activity is detected in the culture liquor. Isolation and purification of XK-62-2 is carried out by a combination of adsorption and desorption from ion exchange resins and active carbon and column chromatography using cellulose, Sephadex, alumina and silica gel. In this manner, XK-62-2 can be obtained in the form of a salt or as a free base.

XK-62-2 has a molecular formula of $C_{20}H_{41}N_5O_7$, and a molecular weight of 463. The substance is freely soluble in water and methanol, slightly soluble in ethanol and acetone and insoluble in chloroform, benzene, ethyl acetate and n-hexane.

SUMMARY OF THE INVENTION

The present invention concerns new antibiotic derivatives represented by the general formulae: (I) and (II):

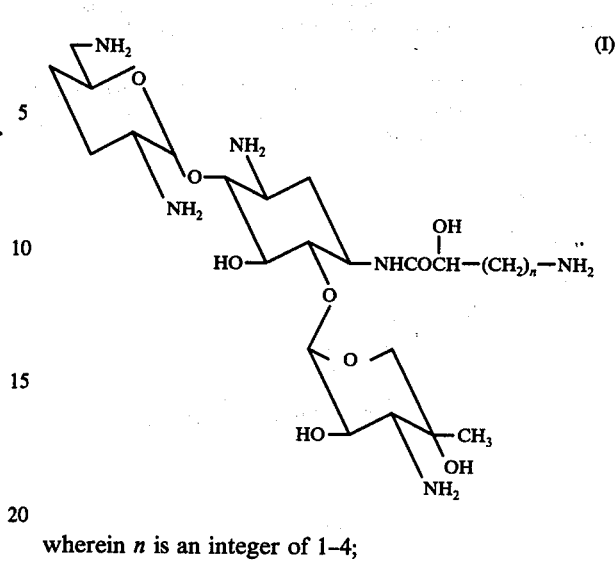

wherein $n$ is an integer of 1–4;

wherein $n$ is an integer of 1–4, and their pharmaceutically-acceptable, acid addition salts.

In addition, the present invention concerns a process for producing the compounds of formula (I) comprising oxidizing compounds of formula (III):

with an oxidizing agent, wherein $R_1$ and $R_2$ represent H or $CH_3$, provided that $R_1$ and $R_2$ are not simultaneously H, and n is an integer of 1–4.

Further, the present invention concerns a process for producing the compounds of formula (II) comprising oxidizing compounds of formula (IV):

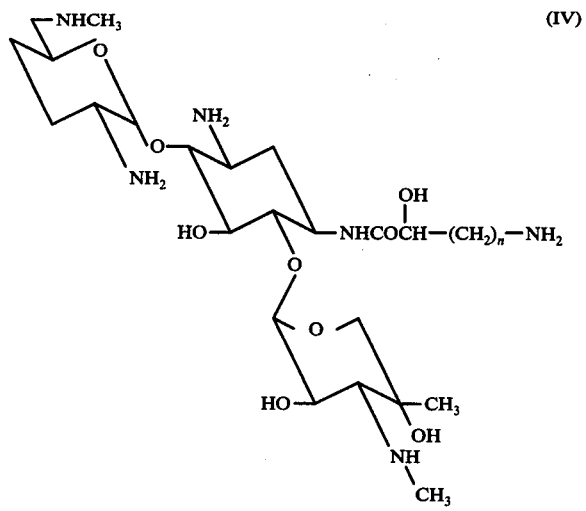

with an oxidizing agent, wherein n is an integer of 1–4.

The compounds of formula (I) of the invention [hereinafter referred to as Compounds (I)] include the following compounds:

Compounds (I-1): 3''-N, 6''-N-didemethyl-1-N-(DL-α-hydroxy-β-aminopropionyl) XK-62-2 (i.e., n = 1)
Compound (I-2): 3''-N, 6'-N-didemethyl-1-N-[L-(−)-α-hydroxy-γ-aminobutyryl] XK-62-2 (i.e., n = 2)
Compound (I-3): 3''-N, 6'-N-didemethyl-1-N-[L-(−)-α-hydroxy-δ-aminovaleryl] XK-62-2 (i.e., n = 3)
Compound (I-4): 3''-N, 6'-N-didemethyl-1-N-[L-(−)-α-hydroxy-ε-aminocaproyl] XK-62-2 (i.e., n = 4)

The compounds of formula (II) of the invention [hereinafter referred to as Compounds (II)] include the following compounds:

Compound (II-1): 3''-N-demethyl-1-N-(DL-α-hydroxy-β-aminopropionyl) XK-62-2 (i.e., n = 1)
Compound (II-2): 3''-N-demethyl-1-N-[L-(−)-α-hydroxy-γ-aminobutyryl] XK-62-2 (i.e., n = 2)
Compound (II-3): 3''-N-demethyl-1-N-[L-(−)-α-hydroxy-δ-aminovaleryl] XK-62-2 (i.e., n = 3)
Compound (II-4): 3''-N-demethyl-1-N-[L-(−)-α-hydroxy-ε-aminocaproyl] XK-62-2 (i.e., n = 4)

Compounds (I) and Compounds (II) are novel antibiotic derivatives which have a strong antibacterial activity against a variety of Gram-positive and Gram-negative bacteria, and particularly against those bacteria that are resistant to known aminoglycoside antibiotics.

DETAILED DESCRIPTION OF THE INVENTION

The Oxidation Reaction

Figure 1:
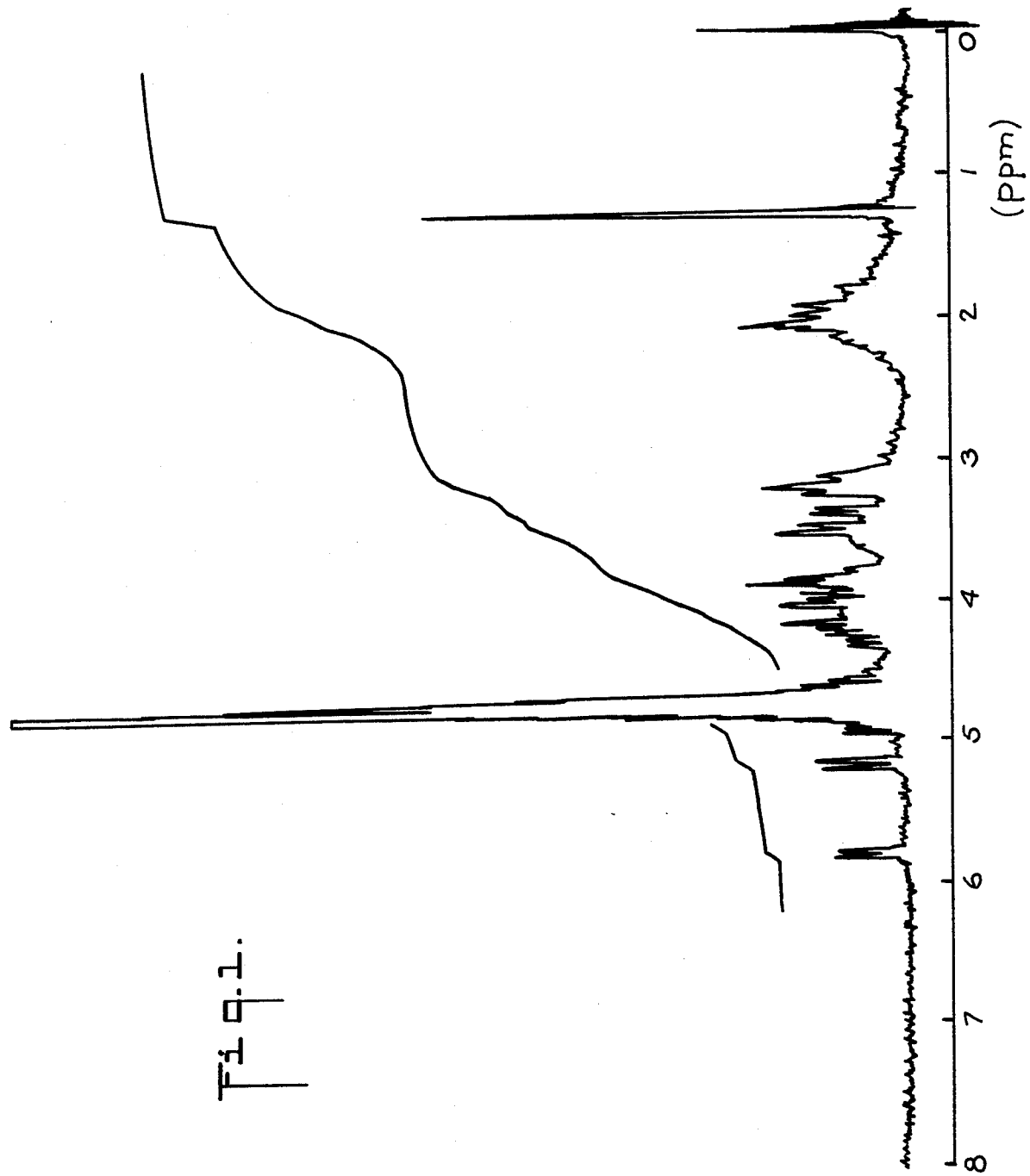
FIG. 1 shows the nuclear magnetic resonance spectrum of 3''-N, 6'-N-didemethyl-1-N-[L-(−)-α-hydroxy-γ-aminobutyryl] XK-62-2 [Compound (I-2)].

The processes for producing Compounds (I) from the compounds of formula (III) [hereinafter referred to as Compounds (III)] and Compounds (II) from the compounds of formula (IV) [hereinafter referred to as Compounds (IV)] may be conducted by a known oxidation reaction using conventional methods and materials.

More specifically, Compounds (I) and (II) can be prepared by reacting Compounds (III) and (IV), respectively, with an oxidizing agent in an appropriate inert solvent under the following conditions. The reaction temperature is −20° to 1010° C, generally 0° to 70° C. The reaction time is 0.5–50 hours. The pH of the reaction mixture is 4.0 – 12.0. These reaction conditions are properly selected within the above ranges according to the kind of the oxidizing agent, the amount of the oxidizing agent and other reaction conditions.

The oxidizing agent to be used in the processes of the present invention includes the conventional oxidizing agents and compounds having potential oxidation ability. Specifically, heavy metal salts, peroxides, halogens, halogenic acids, nitrogen oxides, molecular oxygen, and the like may be used. More specifically, the conventional oxidizing agents such as permanganates, manganates, manganese dioxide, chromic anhydride, bichromates, chromates, alkyl chromates, chromyl chloride, selenium dioxide, cobaltic salts, ceric salts, potassium ferricyanide, cupric oxide, lead oxide, mercuric oxide, mixtures of hydrogen peroxide with one or more of the reagents selected from the group consisting of ferrous salt, ferric salt, selenium dioxide, osmium tetroxide, vanadates, tungstic acid and chromic acid, lead tetraacetate, chlorine, bromine, iodine, hypochlorous acid, chloric acid, hypobromous acid, bromic acid, periodic acid, nitrous oxide, nitrogen monoxide, nitrogen dioxide, air, etc. may be used. Noble metals such as platinum, nickel, palladium, rhodium, ruthenium, rhenium, and the like are preferably employed as a catalyst when molecular oxygen is used.

Although any of the above-mentioned oxidizing agents may be used to accomplish the present invention, chlorine, bromine, iodine, potassium ferricyanide, potassium permanganate and air are preferably used and iodine is most preferably used.

Compounds (III) and (IV) contain functional groups such as hydroxyl groups and amino groups within their molecules. The object of the present invention can be accomplished while avoiding serious loss of these functional groups by properly controlling the amount of the oxidizing agent, the acidity of the reaction mixture, the reaction temperature, the reaction time and the amount of solvent in the reaction with the above-mentioned conventional oxidizing agent.

The amount of the oxidizing agent is 0.5 to 15.0 moles per one mole of the starting Compounds (III) or (IV) but the amount can be properly selected within the above range depending upon the kind of the oxidizing agent, the reaction temperature and other reaction conditions.

Solvents which can dissolve the reactants but are least reactive with them may be used for the present invention. For example, water alone or in combination with one or more solvents selected from methanol, ethanol, tetrahydrofuran, dimethylacetamide, dimethylformamide, dioxane and ethylene glycol dimethyl ether are used.

The starting compound is dissolved in the solvent at a concentration of from 4.5 to 50 m mol.

Preparation of Starting Compounds (III)

The starting Compounds (III) may be prepared as follows: The compounds where $R_1$ and $R_2$ are both $CH_3$ [hereinafter referred to as Compounds (III-a)] can be prepared by introducing the correspondng α-hydroxy-ω-aminoacyl group to the amino group bonded to the carbon atom at the 1-position of the known compound, XK-62-2. Such methods are disclosed in the following copending U.S. patent applications, the disclosures of which are hereby expressly incorporated herein by reference:

| Serial No. | Filing Date   | n                      |
|------------|---------------|------------------------|
| 531,768    | Dec. 11, 1974 | 2, now abandoned       |
| 531,769    | Dec. 11, 1974 | 2, now abandoned       |
| 542,950    | Jan. 22, 1975 | 2, Pat. No. 4,055,715  |
| 556,223    | Mar. 7, 1975  | 1, now abandoned       |
| 601,361    | Aug. 4, 1975  | 3,4                    |

Briefly, the Compounds (III-a) can be prepared by first protecting the amino groups bonded to the carbon atoms at the 2'- and/or 6'-positions of XK-62-2, then reacting the resulting compound with an acylating agent, i.e. a compound capable of introducing an α-hydroxy-ω- substituted aminoacyl group wherein at least one of the hydrogen atoms of the ω-amino group is substituted by a protecting group to introduce the α-hydroxy-ω-substituted aminoacyl group into the amino group bonded to the carbon atom at the 1-position of the compound, and finally removing all of the amino protecting groups. Generally, any readily eliminable protecting group usually used in peptide synthesis may be used, and the conditions of reaction can be those usually employed in known amino-protecting reactions. Typical protecting groups and the corresponding reagents are described in M. Bodanszky et al: *Peptide, Synthesis*, pages 21–41 and 75–135, (1966) (John Wiley & Sons, Inc., U.S.A.) (hereinafter referred to as document A); A. Kapoor: Journal of Pharmaceutical Sciences, Vol. 59, pages 1–27 (1970) (hereinafter referred to as document B); and in M. Bodanszky et al: *Synthesis*, pages 453–463 (1972) (hereinafter referred to as document C).

Examples of the preferred protecting groups and the corresponding reagents are shown below.

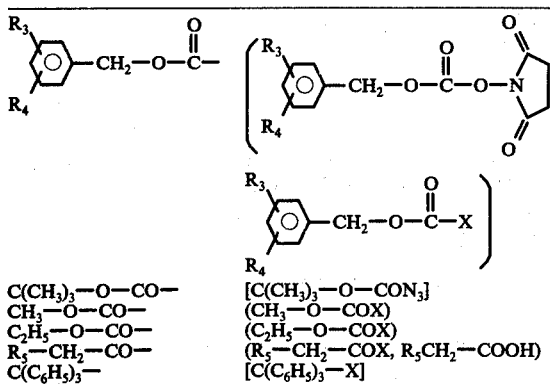

C(CH₃)₃—O—CO—
CH₃—O—CO—
C₂H₅—O—CO—
R₅—CH₂—CO—
C(C₆H₅)₃—

[C(CH₃)₃—O—CON₃]
(CH₃—O—COX)
(C₂H₅—O—COX)
(R₅—CH₂—COX, R₅CH₂—COOH)
[C(C₆H₅)₃—X]

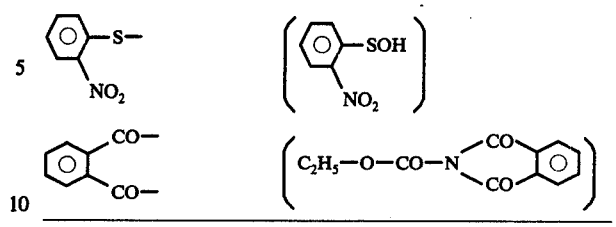

[$R_3$ and $R_4$ in the above formulae may be the same or different and are H, OH, $NO_2$, Cl, Br, I, alkyl groups having 1 to 5 carbon atoms or alkoxy groups having 1 to 5 carbon atoms, $R_5$ is H, F, Cl, Br, I or an alkyl group having 1 to 5 carbon atoms and X is Cl, Br or I].

More specifically, one mole of XK-62-2 is reacted with 1.0 to 4.5 moles, preferably 1.5 to 2.6 moles, of the protecting reagent at a temperature of from −50° to 50° C, preferably −20° to 30° C, in an appropriate solvent. Suitable solvents are water; alcohols such as methanol, ethanol, 2-propanol, butanol, etc.; amides such as dimethylformamide, dimethylacetamide, etc.; tetrahydrofuran; dioxane; ethylene glycol dimethyl ether; pyridine; mixtures thereof; etc. A mixed solvent of ethanol and water (2:1 by volume) is especially preferred. The foregoing process per se is described in documents A, B and C above.

The resulting compound is then reacted with an acylating agent, i.e. a compound capable of introducing an α-hydroxy-ω-substituted aminoacyl group wherein at least one of the hydrogen atoms of the ω-amino group is substituted by a protecting group or functional derivatives thereof. The functional derivative of the carboxyl group of the agent can be any of various known functional derivatives at carbonyl groups usually used in peptide synthesis, such as acid halides, acid azide, mixed acid anhydrides, and reactive esters; and specific examples are described in the aforementioned documents A, B and C.

As preferred functional derivatives, those having a structure in which the hydroxy group of the carboxyl group is substituted by one of the following groups are appropriate:

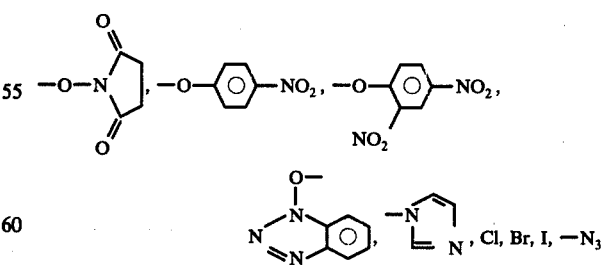

or $R_6OCOO$— wherein $R_6$ is an alkyl group having 1 to 7 carbon atoms or a phenyl group.

Particularly preferred acylating agents are those having a structure in which the OH group of the carboxyl group is substituted by

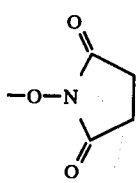

These compounds are prepared by reacting the corresponding α-hydroxy-ω-substituted amino acid with N-hydroxysuccinimide in the presence of a dehydrating and condensing agent such as dicyclohexylcarbodiimide.

The resulting reaction mixture containing the acylating agent can be used for the acylating reaction as is, although the acylating agent may be isolated from the reaction mixture, then used for the acylating reaction.

Other acylating agents may, of course, be used in the same manner as above.

As the solvent for the acylating reaction, any of the solvents mentioned above in connection with the amino-protecting reaction can be used.

This acylating method per se is described in the aforementioned documents A, B and C.

The amino protecting groups of the resulting derivative of XK-62-2 obtained by the acylating reaction can be eliminated in the known manner of eliminating amino protecting groups. For example, when the amino protecting groups are phthaloyl groups, elimination is accomplished with hydrazine; when the amino protecting groups are carbomethoxy groups or carboethoxy groups, elimination is accomplished with barium hydroxide; when the amino protecting groups are tertiary butoxycarbonyl groups, elimination is accomplished with formic acid or trifluoroacetic acid; when the amino protecting groups are trityl groups, elimination is accomplished with acetic acid or trifluoroacetic acid; when the amino protecting groups are orthonitrophenylsulphenyl groups, elimination is accomplished with acetic acid or hydrochloric acid; and when the amino protecting groups are chloroacetyl groups, elimination is accomplished with 3-nitropyridine-2-thione [reported by K. Undheim et al: *Journal of the Chemical Society, Perkin Transactions Part I*. page 829 (1973)].

When the amino protecting groups are benzyloxycarbonyl groups, elimination is easily carried out by a hydrogenolysis at room temperature under atmospheric pressure with a small amount of acid such as hydrochloric acid, hydrobromic acid, hydriodic acid, acetic acid, etc. in the presence of a metal catalyst such as palladium, platinum and so on, in at least one solvent selected from the group consisting of water, alcohols, tetrahydrofuran, dioxane, dimethylformamide, dimethylacetamide, ethylene glycol dimethyl ether, etc.

The desired product may be isolated and purified from the thus obtained reaction mixture by employing either column chromatography using adsorbents such as ion exchange resins, silica gel, alumina, cellulose, Sephadex, etc., or thin layer chromatography using silica gel, alumina or cellulose.

The starting Compounds (III) where $R_1$ is H and $R_2$ is $CH_3$ [hereinafter referred to as Compounds (III-c)] may be prepared in the same manner as Compounds (III-a) as set forth above by acylating 6'-N-demethyl XK-62-2 (which is gentamicin $C_{1a}$ whose preparation is set forth in U.S. Pat. No. 3,091,572, the disclosure of which is hereby expressly incorporated herein by reference).

The starting Compounds (III) where $R_1$ is $CH_3$ and $R_2$ is H [hereinafter sometimes referred to as Compounds (III-b)] are the same as Compounds (II), and can be prepared by the oxidation process of the present invention.

Preparation of Starting Compounds (IV)

Compounds (IV) are the same as Compounds (III-a) and can be prepared as set forth hereinabove.

Production of Compounds (I)

When Compounds (III-a) are oxidized as described above, a mixture of Compounds (III-b), (III-c) and (I) is obtained. The desired product, Compounds (I), can be obtained from this mixture. Further, Compounds (I) can be obtained by isolating Compounds (III-b) and (III-c) from the mixture and oxidizing them. In order to obtain the desired product, Compounds (I), in a high yield from Compounds (III), the use of Compounds (III-c) is preferred, since the N-methyl group bonded to the carbon atom at the 3"-position of Compounds (III) is more reactive than that bonded to the carbon atom at the 6'-position.

In preparing Compounds (I), the reaction conditions when iodine, which is the most preferred oxidizing agent, is used are explained in detail as follows.

(A) Synthesis of Compounds (III-b) from Compounds (III-a)

Usually, 0.7 to 10.0 moles, preferably 2.0 to 6.0 moles, of iodine is used per one mole of Compounds (III-a) to obtain Compounds (III-b) by eliminating the methyl group of the N-methyl group bonded to the carbon atom at the 3"-position of Compounds (III-a).

The desired Compounds (III-b) can be obtained in a high yield by keeping the pH of the reaction mixture basic during this reaction. As the basic substance used to keep the reaction mixture basic, those which do not react with the starting compounds, the oxidizing agent and the reaction products are appropriate. For example, hydroxides and carbonates of alkali metals and alkaline earth metals, alcoholates of alkali metals, alkali metal salts of carboxylic acid and alkaline earth metal salts of carboxylic acid may be used. As for the amount of the basic substance, 0.5 to 6.0 moles, preferably 1.5 to 3.5 moles, of a strongly basic substance or 5.0 to 25.0 moles, preferably 5.0 to 13.0 moles, of a weakly basic substance is used per one mole of the material which is to be demethylated. These basic substances may be added at the start of the reaction or added intermittently during the reaction and there is no substantial difference between these two ways.

The reaction is carried out generally at a temperature of −10° to 90° C, preferably at 20° to 50° C, and is completed in 1 to 24 hours, generally 2 to 15 hours.

(B) Synthesis of Compounds (III-c) from Compounds (III-a)

This reaction is carried out under the same conditions as in (A) except that usually, 1.0 to 13.0 moles, preferably 4.0 to 8.0 moles, of iodine is used per one mole of Compounds (III-a).

(C) Synthesis of Compounds (I) from Compounds (III-a)

This reaction is carried out under the same conditions as in (A) except that usually, 2.0 to 15.0 moles, preferably 6.0 to 11.0 moles, of iodine is used per one mole of Compounds (III-a).

(D) Synthesis of Compounds (I) from Compounds (III-b)

The desired Compounds (I) can be obtained under the same conditions as in (A) except that Compounds (III-b) are used as the starting materials and that 2.0 to 15.0 moles, preferably 6.0 to 11.0 moles of iodine is used per one mole of Compounds (III-b).

(E) Synthesis of Compounds (I) from Compounds (III-c)

The desired Compounds (I) can be obtained under the same conditions as in (A) except that Compounds (III-c) are used as the starting materials and that usually, 0.7 to 10.0 moles, preferably 2.0 to 6.0 moles of iodine is used per one mole of Compounds (III-c).

In the above reactions, the reaction mixture containing Compounds (III-b) and (III-c) produced from Compounds (III-a) can be used directly for the preparation of Compounds (I) without the necessity for isolating and recovering Compounds (III-b) and (III-c).

Isolation and purification of the products from the reaction mixture is preferably carried out in the following manner.

After the completion of reaction, the reaction mixture is neutralized. The neutralized reaction mixture is contacted with a cation exchange resin as is, or is concentrated under reduced pressure and an aqueous solution of the resulting residue is contacted with a cation exchange resin. The unreacted starting material and the reaction products are adsorbed on the resin. Thereafter, the resin is washed with water and elution is carried out with 2.0N aqueous ammonia. After the eluate is concentrated, the products are isolated and purified by conventional methods, for example, column chromatography and thin layer chromatography using adsorbents such as ion exchange resins, silica gel, alumina, cellulose, etc.

Preparation of Compounds (II)

In preparing Compounds (II), when iodine which is the most preferred oxidizing agent is used as the oxidizing agent, the reaction conditions are as follows.

In order to efficiently produce Compounds (II) by eliminating the methyl group of the N-methyl group bonded to the carbon atom at the 3''-position of Compounds (IV), iodine is used as the oxidizing agent in an amount of 0.7 to 10.0 moles, preferably 2.0 to 6.0 moles, per one mole of Compounds (IV).

The desired Compounds (II) can be obtained in high yields by maintaining the reaction mixture at a basic pH when iodine is used as the oxidizing agent. As the basic substances to be used for the maintenance of the reaction mixture at a basic pH during the reaction, those which have only a remote possibility of decomposing Compounds (IV) and their demethylated products by reacting with them and of substantially reducing the reactivity of iodine by reacting with iodine are desirable. For example, hydroxides and carbonates of alkali metals and alkaline earth metals, alcoholates of alkali metals, alkali metal salts of carboxylic acids and alkaline earth metal salts of carboxylic acids are the basic substances which satisfy the above requirements.

As for the amount of the basic substances, 0.5 to 6.0 moles, preferably 1.5 to 3.5 moles, of a strongly basic substance is used per one mole of the compound to be demethylated or 5.0 to 25.0 moles, preferably 5.0 to 13.0 moles, of a weakly basic substance is used per one mole of the compound to be demethylated. These basic substances may be added either at the start of the reaction or intermittently during the reaction without any substantial difference.

The reaction temperature is generally −10° to 90° C, preferably 20° to 50° C, and the reaction is complete in 1 to 24 hours, usually 2 to 15 hours.

In the process of the present invention, Compounds (II) are hardly produced selectively; but compounds wherein the methyl group of the N-methyl group bonded to the carbon atom at the 6'-position of Compounds (IV) is eliminated [corresponding to Compounds (III-c)] and compounds wherein the methyl groups of the N-methyl groups bonded to the carbon atoms at both the 6'- and 3''-positions of Compounds (IV) are eliminated [resulting in Compounds (I)] are produced simultaneously with the production of Compounds (II).

Isolation and purification of the product from the reaction mixture is preferably carried out in the same manner as described above in the preparation of Compounds (I).

Antibacterial Activity

Compounds (I) and (II), which are the desired compounds of the present invention, are novel antibiotic derivatives and have per se an antibacterial activity. Therefore, they are useful as antibiotics.

Table 1 shows antibacterial spectra of 1-N-[DL-(α-hydroxy-β-aminopropionyl)] XK-62-2, 1-N-[L-(−)-α-hydroxy-γ-aminobutyryl] XK-62-2, Compounds (I-1), (I-2), (II-1) and (II-2) against various Gram-negative and Gram-positive bacterial determined by agar dilution method at pH 7.2.

Table 1

| Strains | 1-N-(DL-α-hydroxy-β-aminopropionyl XK-62-2 | 1-N-[L-(-)-α-hydroxy-γ-aminobutyryl] XK-62-2 | Compound I-1 | Compound I-2 | Compound II-1 | Compound II-2 |
|---|---|---|---|---|---|---|
| *Staphylococcus aureus* 209 P | 0.4 | 0.4 | 0.2 | 0.2 | 0.4 | 0.4 |
| *Staphylococcus aureus* Smith | 0.2 | 0.1 | 0.2 | 0.2 | 0.4 | 0.4 |
| *Streptococcus faecalis* ATCC 10541 | 12.5 | 6.25 | 12.5 | 12.5 | 25 | 25 |
| *Bacillus subtilis* ATCC 6633 | 0.2 | 0.1 | 0.1 | 0.1 | 0.2 | 0.2 |
| *Sarcina lutea* ATCC 9341 | 0.4 | 0.2 | 0.78 | 0.78 | 1.56 | 1.56 |
| *Escherichia coli* T-2 | 0.4 | 0.4 | 1.56 | 0.78 | 1.56 | 0.78 |
| *Escherichia coli* T-5 | 0.78 | 0.4 | 1.56 | 1.56 | 1.56 | 0.4 |
| *Escherichia coli* Juhl | 0.78 | 0.4 | 1.56 | 1.56 | 3.12 | 1.56 |
| *Pseudomonas aeruginosa* BMH 1 | 1.56 | 0.78 | 0.78 | 0.78 | 1.56 | 1.56 |
| *Pseudomonas aeruginosa* BMH 10 | 0.4 | 0.4 | 0.4 | 0.4 | 0.4 | 0.4 |
| *Pseudomonas aeruginosa* No. 12 | 0.78 | 0.4 | 0.4 | 0.4 | 0.78 | 0.78 |
| *Pseudomonas aeruginosa* NC-5 | 3.12 | 3.12 | 0.78 | 1.56 | 3.12 | 3.12 |
| *Pseudomonas aeruginosa* E-2 | 3.12 | 3.12 | 1.56 | 1.56 | 3.12 | 3.12 |
| *Klebsiella pneumoniae* No. 8045 | 0.78 | 0.2 | 0.4 | 0.78 | 0.78 | 0.78 |
| *Salmonella enteritidis* G-14 | 6.25 | 3.12 | 6.25 | 12.5 | 3.12 | 3.12 |

Table 1-continued

| Strains | 1-N-(DL-α-hydroxy-β-aminopropionyl XK-62-2 | 1-N-[L-(-)-α-hydroxy-γ-aminobutyryl] XK-62-2 | Compound I-1 | Compound I-2 | Compound II-1 | Compound II-2 |
|---|---|---|---|---|---|---|
| Salmonella typhimurium E-9 | 0.4 | 0.2 | 0.78 | 0.4 | 0.78 | 0.78 |
| Shigella sonnei ATCC 9290 | 0.78 | 0.78 | 3.12 | 1.56 | 3.12 | 3.12 |
| Serratia sp T-55 | 1.56 | 0.78 | 3.12 | 3.12 | 1.56 | 1.56 |
| Proteus mirabilis 1287 | 12.5 | 12.5 | 12.5 | 12.5 | 25 | 12.5 |
| Proteus vulgaris 6897 | 12.5 | 1.56 | 6.25 | 3.12 | 12.5 | 6.25 |
| Proteus rettgeri KY 4288 | 1.56 | 0.78 | 0.78 | 0.78 | 1.56 | 0.78 |
| Proteus morganii KY 4298 | 0.78 | 0.78 | 1.56 | 0.78 | 3.12 | 1.56 |
| Escherichia coli KY Z-343[1] | 0.2 | 0.1 | 0.4 | 0.2 | 0.4 | 0.2 |
| Escherichia coli KY 8348[2] | 0.2 | 0.1 | 0.4 | 0.4 | 0.4 | 0.4 |
| Escherichia coli KY 8320[3] | 0.4 | 0.2 | 0.78 | 0.78 | 1.56 | 0.78 |
| Escherichia coli KY 8349[3] | 0.1 | 0.1 | 0.4 | 0.4 | 0.4 | 0.4 |
| Escherichia coli KY Z-338[4] | 0.2 | 0.2 | 0.78 | 0.4 | 0.78 | 0.4 |
| Escherichia coli KY 8321[5] | 0.4 | 0.2 | 1.56 | 0.78 | 1.56 | 0.78 |
| Pseudomonas aeruginosa KY 8510[1] | 3.12 | 3.12 | 12.5 | 12.5 | 3.12 | 3.12 |
| Pseudomonas aeruginosa KY 8516[1] | 3.12 | 3.12 | 50 | 25 | 3.12 | 3.12 |
| Pseudomonas aeruginosa KY 8511[2] | 1.56 | 1.56 | 0.78 | 0.78 | 1.56 | 1.56 |
| Pseudomonas aeruginosa KY 8518[3] | 1.56 | 1.56 | 0.78 | 0.78 | 1.56 | 1.56 |
| Pseudomonas aeruginosa KY 8512[6] | 1.56 | 1.56 | 0.78 | 0.78 | 1.56 | 1.56 |
| Pseudomonas aeruginosa KY 8519[6] | 6.25 | 6.25 | 3.12 | 3.12 | 6.25 | 6.25 |
| Pseudomonas aeruginosa KY 8563[7] | 3.12 | 6.25 | 1.56 | 3.12 | 3.12 | 3.12 |
| Pseudomonas aeruginosa KY Z-444[8] | 1.56 | 1.56 | 1.56 | 1.56 | 1.56 | 1.56 |
| Pseudomonas aeruginosa KY Z-445[8] | 3.12 | 6.25 | 6.25 | 6.25 | 6.25 | 6.25 |
| Serratia marcescens POE 1065[1] | 0.78 | 0.78 | 50 | 25 | 3.12 | 3.12 |
| Providencia sp. 164[9] | 6.25 | 6.25 | 6.25 | 6.25 | 25 | 12.5 |
| Klebsiella pneumoniae Y-58[4] | 0.4 | 0.2 | 0.78 | 0.78 | 0.78 | 0.4 |
| Klebsiella pneumoniae Y-60[4] | 0.4 | 0.2 | 0.78 | 0.78 | 1.56 | 0.78 |

[1] produces kanamycin acetyltransferase
[2] produces gentamicin acetyltransferase Type I
[3] produces neomycin-kanamycin phosphotransferase Type I
[4] produces gentamicin adenyltransferase
[5] produces gentamicin adenyltransferase and neomycin-kanamycin phosphotransferase Type II
[6] produces neomycin-kanamycin phosphotransferase Type I and Type II
[7] produces gentamicin acetyltransferase Type III
[8] produces 6'-N-acetyltransferase Type III
[9] produces gentamicin acetyltransferase Type II
The foregoing enzymes are produced intracellularly and, with the enzymes, the bacteria inactivate antibiotics.

From the foregoing Table 1, it is apparent that Compounds (I) and (II) show a remarkably strong antibacterial activity against a variety of Gram-positive bacteria and Gram-negative bacteria including those resistant to aminoglycoside antibiotics. Therefore, they are expected to be effective for the treatment of various infections in humans and in animals induced by such phlogogenous bacteria. For example, these compounds are expected to be effective for the treatment of urinary tract infections and respiratory infections induced by *Staphylococcus aureaus, Escherichia coli* and strains of the genus Proteus. The compounds are also useful for sterilization of surfaces such as in hospitals and areas of food preparation.

Table 2 shows the acute toxicity (LD$_{50}$) of 1-N-(DL-α-hydroxy-β-aminopropionyl) XK-62-2, 1-N-[L-(−)-α-hydroxy-γ-aminobutyryl] XK-62-2, Compounds (I-2), (II-1) and (II-2) in mice.

Table 2

| | LD$_{50}$ mg/kg |
|---|---|
| 1-N-(DL-α-hydroxy-β-aminopropionyl)-XK-62-2 | 185 |
| 1-N-[L-(-)-α-hydroxy-γ-aminobutyryl]-XK-62-2 | 180 |
| Compound (I-2) | 200 |
| Compound (II-1) | 175 |
| Compound (II-2) | 250 |

If desired, the desired Compounds (I) and (II) of the present invention can be converted to their addition salts (that is amine salts) with pharmaceutically acceptable non-toxic acids. In the present invention, the non-toxic acids include inorganic acids such as hydrochloric acid, hydrobromic acid, hydriodic acid, sulfuric acid, phosphoric acid, carbonic acid, etc. and organic acids such as acetic acid, fumaric acid, malic acid, citric acid, mandelic acid, tartaric acid, ascorbic acid, etc. The acid addition salts are prepared by methods well known to the art.

The practice of the present invention is illustrated by the following representative examples. However, various modifications are possible and the examples are not limitative of the invention.

EXAMPLE 1

720 mg (1.28 mmoles) of 1-N-[L-(−)-α-hydroxy-γ-aminobutyryl] XK-62-2 and 2.10 g (15.4 mmoles) of sodium acetate trihydrate are dissolved in 55.0 ml of aqueous 50% dimethylformamide. To the solution is added 1.8 g (7.1 mmoles) of iodine at one time. Reaction is carried out with stirring at 55° C for 2.5 hours. After the completion of reaction, the reaction mixture is passed through a column of 50 ml of Amberlite (product of Rohm & Haas Co.) IRC-50 (H$^+$ form) and the column is washed with 200 ml of water for desalting and decoloring. Thereafter, 2.0N aqueous ammonia is passed through the column. 85 ml of the fractions which show positive coloring reaction with ninhydrin are combined and concentrated under reduced pressure to obtain 670 mg of a slightly yellowish residue. The residue is subjected to column chromatography using 25 g of silica gel and a solvent of isopropanol:chloroform::concentrated aqueous ammonia = 4:1:1 by volume. The eluate is taken in 12 ml portions. Fraction Nos. 35–55 are combined and concentrated to dryness under reduced pressure to recover 210 mg of the unreacted starting material.

Then, fraction Nos. 61–69 are concentrated to dryness under reduced pressure to obtain 54 mg of 6'-N- demethyl-1-N-[L-(—)-α-hydroxy-γ-aminobutyryl] XK-62-2.

Thereafter, fraction Nos. 73–101 are concentrated under reduced pressure to obtain 175 mg of 3''-N-demethyl-1-N-[-(—)-α-hydroxy-γ-aminobutyryl] XK-62-2 [i.e., Compound (II-2)].

Rf values of Compound (II-2) and the starting compound in silica gel thin layer chromatography [plate: silica gel No. 5715 (produced by Merck & Co., Inc.), developer:n-butanol:ethanol:chloroform:concentrated aqueous ammonia = 4:5:2:5 by volume, developed at room temperature for 4 hours] are 0.28 and 0.33 respectively.

Figure 2:
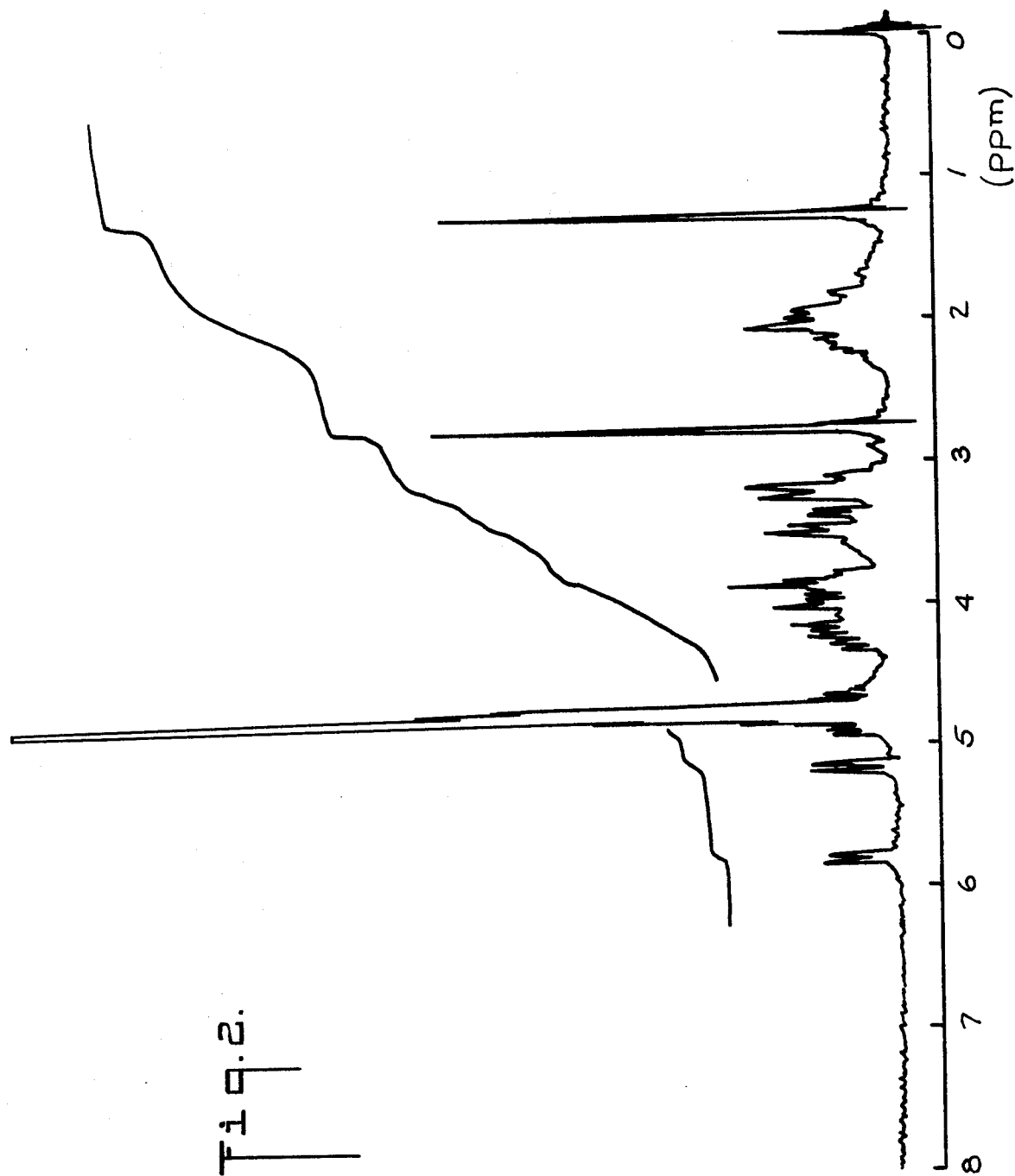
FIG. 2 shows the nuclear magnetic resonance spectrum of 3''-N-demethyl-1-N-[L-(−)-α-hydroxy-γ-aminobutyryl] XK-62-2 [Compound (II-2)].

Melting point: 138°–157° C
Specific rotation: $[\alpha]_D^{29}$ + 89.6 (c = 1.05, water)
Infrared absorption spectrum: $\nu_c$ = 0 1640 cm$^{-1}$
Nuclear magnetic resonance spectrum (in $D_2O$, pD = 0.9) δ (in p.p.m. from DSS) (FIG. 2): 1.29(3H, s), 2.29(3H, s), 5.18(1H, d, J = 4.0 Hz) 5.81(1H, d, J = 3.5 Hz)
Elementary analysis: Calculated for $C_{23}H_{46}N_6O_9 \cdot H_2O$: C = 48.58%, H = 8.51%; N = 14.78%. Found: C = 48.97%; H = 8.15%; N = 14.52%

Fraction Nos. 109–137 are concentrated to dryness under reduced pressure to obtain 98 mg of 3''-N, 6'-N-didemethyl-1-N-[L-(—)-α-hydroxy-γ-aminobutyryl] XK-62-2 [i.e., Compound (I-2)].

Rf value of Compound (I-2) obtained from silica gel thin layer chromatography under the same conditions as in the above chromatography of Compound (II-2) and the starting compound is 0.22.

Melting point: 136°–153° C
Specific rotation: $[\alpha]_3^{29}$ + 89.9° (c = 0.57, water)
Infrared absorption spectrum: $\nu_c$ = 0 1640 cm$^{-1}$
Nuclear magnetic resonance spectrum: (in $D_2O$, pD = 1.0) δ (in p.p.m. from DSS) (FIG. 1): 1.28 (3H, s), 5.18(1H, d, J = 3.7 Hz) 5.66 (1H, d, J = 3.5 Hz)
Elementary analysis: Calculated for $C_{22}H_{44}N_6O_9 \cdot H_2O$: C = 47.64%; H = 8.36%; N = 15.15%. Found: C = 48.01%; H = 8.72%; N = 15.42%.

EXAMPLE 2

169.4 mg (0.3 mmole) of 1-N-[L-(—)-α-hydroxy-γ-aminobutyryl] XK-62-2 and 24.0 mg (0.6 mmole) of sodium hydroxide are dissolved in 15 ml of aqueous 50% dimethylacetamide. To the solution is added 98.8 mg (0.6 mmole) of potassium ferricyanide at one time and the mixture is allowed to react with stirring at 30° C overnight. After the completion of reaction, the reaction mixture is passed through a column of 20 ml of Amberlite IRC-50 (H+ form). The column is washed with 100 ml of water. Thereafter, 2.0N aqueous ammonia is passed through the column. 25 ml of fractions which show positive coloring reaction with ninhydrin are combined and concentrated under reduced pressure to obtain 163 mg of a slightly yellowish residue. The thus obtained residue is subjected to silica gel column chromatography in the same manner as in the above Example 1. As the result, 53 mg of the unreacted starting material is recovered and subsequently 18 mg of 6'-N-demethyl-1-N-[L-(—)-α-hydroxy-γ-aminobutyryl] XK-62-2, 42 mg of Compound (II-2) and 9 mg of Compound (I-2) are obtained.

EXAMPLE 3

282.4 mg (0.5 mmole) of 1-N-([L-(—)-α-hydroxy-γ-aminobutyryl] XK-62-2 is dissolved in 20 ml of water and to the solution is added 350 mg of fresh platinum black previously activated by hydrogen. The mixture is allowed to react for 30 hours while maintaining the temperature at 50° C and vigorously introducing air to the reaction mixture as fine bubbles. After the completion of reaction, platinum black is removed by filtration. The filtrate is concentrated under reduced pressure to obtain 275 mg of a residue. The residue is subjected to silica gel column chromatography in the same manner as in the above Example 1. As the result, 137 mg of the unreacted starting material is recovered and subsequently 23 mg of 6'-N-demethyl-1-N-[L-(—)-α-hydroxy-γ-aminobutyryl] XK-62-2, 73 mg of Compound (II-2) and 11 mg of Compound (I-2) are obtained.

EXAMPLE 4

112.9 mg (0.2 mmole) of 1-N-[L-(—)-α-hydroxy-γ-aminobutyryl] XK-62-2 is dissolved in 10 ml of water and to the solution is added 189.6 mg (1.2 mmoles) of potassium permanganate. The mixture is allowed to react at room temperature overnight. After the completion of reaction, the reaction mixture is passed through the column of 15 ml of Amberlite IRC-50 (H+ form). Then, the column is washed with 100 ml of water and 2.0N aqueous ammonia is passed through the column. 30 ml of fractions which show positive coloring reaction with ninhydrin are combined and concentrated under reduced pressure to obtain 108 mg of a slightly yellowish residue. The residue is subjected to silica gel column chromatography in the same manner as in the above Example 1. As the result, 29 mg of the unreacted starting material is recovered and subsequently 8 mg of 6'-N-demethyl-1-N-[L-(—)-α-hydroxy-γ-aminobutyryl] XK-62-2, 27 mg of Compound (II-2) and 13 mg of Compound (I-2) are obtained.

EXAMPLE 5

568.7 mg (1.0 mmole) of Compound (II-2) is dissolved in 4.0 ml of water. To the solution is added a solution obtained by dissolving 98 mg (1.0 mmole) of sulfuric acid in 1.0 ml of water under cooling. After 30 minutes, cold ethanol is added to the mixture until precipitation is complete. Upon filtration of the mixture containing a precipitated white solid, the monosulfate of Compound (II-2) is obtained.

EXAMPLE 6

170.6 mg (0.3 mmole) of Compound (II-2) and 408.3 mg (3.0 mmoles) of sodium acetate trihydrate are dissolved in 15 ml of aqueous 50% tetrahydrofuran. To the solution is added 456.9 mg (1.8 mmoles) of iodine and the mixture is allowed to react at 45° C with stirring for 40 hours. After the completion of reaction, the reaction mixture is treated in the same manner as in Example 1. As the result, 75 mg of unreacted Compound (II-2) is recovered and subsequently, 35 mg of Compound (I-2) is obtained.

EXAMPLE 7

113.7 mg (0.2 mmole) of Compound (II-2) and 16 mg (0.4 mmole) of sodium hydroxide are dissolved in 10 ml of aqueous 50% dimethylacetamide. To the solution is added, at a time, 131.7 mg (0.4 mmole) of potassium ferricyanide and the mixture is allowed to react at 30° C with stirring for 5.0 hours. After the completion of reaction, the reaction mixture is treated in the same manner as in Example 2. As the result, 41 mg of unreacted Compound (II-2) is recovered and subsequently, 23 mg of Compound (I-2) is obtained.

EXAMPLE 8

150 mg (0.26 mmole) of Compound (II-2) is dissolved in 10 ml of water and to the solution is added 210 mg of fresh platinum black previously activated by hydrogen. Then, reaction is carried out for 30 hours while keeping the temperature at 50° C and vigorously introducing fine air bubbles to the reaction mixture. After the completion of reaction, the reaction mixture is treated in the same manner as in Example 3. As the result, 81 mg of unreacted Compound (II-2) is recovered and subsequently, 36 mg of Compound (I-2) is obtained.

EXAMPLE 9

120 mg (0.21 mmole) of Compound (II-2) is dissolved in 8 ml of water and to the solution is added 199.1 mg (1.26 mmoles) of potassium permanganate. The mixture is allowed to react at room temperature for 15 hours. After the completion of reaction, the reaction mixture is treated in the same manner as in Example 4. As the result, 39 mg of unreacted Compound (II-2) is recovered and subsequently, 21 mg of Compound (I-2) is obtained.

EXAMPLE 10

113.7 mg (0.2 mmole) of 6'-N-demethyl-1-N-[L-(—)-α-hydroxy-γ-aminobutyryl] XK-62-2 and 272.2 mg (2.0 mmoles) of sodium acetate trihydrate are dissolved in 13 ml of aqueous 50% tetrahydrofuran. To the solution is added 203.1 mg (0.8 mmole) of iodine and the mixture is allowed to react at 40° C with stirring for 3.0 hours. After the completion of reaction, the reaction mixture is treated in the same manner as in Example 1. As the result, 29 mg of the unreacted starting material is recovered and subsequently, 63 mg of Compound (I-2) is obtained.

EXAMPLE 11

113.7 mg (0.2 mmole) of 6'-N-demethyl-1-N-[L-(—)-α-hydroxy-γ-aminobutyryl] XK-62-2 and 14 mg (0.35 mmole) of sodium hydroxide are dissolved in 10 ml of aqueous 50% dimethylacetamide. To the solution is added, at a time, 115.2 mg (0.35 mmole) of potassium ferricyanide and the mixture is allowed to react at 35° C with stirring for 5.0 hours. After the completion of reaction, the reaction mixture is treated in the same manner as in Example 2. As the result, 27 mg of the unreacted starting material is recovered and 48 mg of Compound (I-2) is obtained.

EXAMPLE 12

130 mg (0.23 mmole) of 6'-N-demethyl-1-N-[L-(—)-α-hydroxy-γ-aminobutyryl] XK-62-2 is dissolved in 10 ml of water and to the solution is added 180 mg of fresh platinum black previously activated by hydrogen. Then, reaction is carried out for 30 hours while keeping the temperature at 50° C and vigorously introducing fine air bubbles to the reaction mixture. After the completion of reaction, the reaction mixture is treated in the same manner as in Example 3. As the result, 44 mg of the unreacted starting material is recovered and subsequently, 52 mg of Compound (I-2) is obtained.

EXAMPLE 13

143 mg (0.25 mmole) of (6'-N-demethyl-1-N-[L-(—)-α-hydroxy-γ-aminobutyryl] XK-62-2 is dissolved in 10 ml of water and to the solution is added 197.5 mg (1.25 mmoles) of potassium permanganate. The mixture is allowed to react at room temperature for 15 hours. After the completion of reaction, the reaction mixture is treated in the same manner as in Example 4. As the result, 37 mg of the unreacted starting material is recovered and subsequently, 46 mg of Compound (I-2) is obtained.

EXAMPLE 14

554.7 mg (1.0 mmole) of Compound (I-2) is dissolved in 4.0 ml of water. To the solution is added a solution of 98 mg (1.0 mmole) of sulfuric acid in 1.0 ml of water under cooling. After 30 minutes, cold ethanol is added to the solution until precipitation is complete. By filtering the mixture containing the precipitated white solid, the monosulfate of Compound (I-2) is obtained.

EXAMPLE 15

550 mg (1.0 mmole) of 1-N-(DL-α-hydroxy-β-aminopropionyl) XK-62-2 and 2.10 g (15.4 mmoles) of sodium acetate trihydrate are dissolved in 70 ml of aqueous 50% dimethylformamide. To the solution is added, at a time, 1.8 g (7.1 mmoles) of iodine and the mixture is allowed to react at 55° C with stirring for 5 hours. Then, the reaction mixture is passed through the column packed with 50 ml of Amberlite IRC-50 ($H^+$ form). After the column is washed with 200 ml of water for complete desalting and decoloring, 2.0N aqueous ammonia is passed through the column. About 100 ml of fractions which show positive coloring reaction with ninhydrin are combined and concentrated under reduced pressure to obtain 510 mg of a slightly yellowish residue. The thus obtained residue is subjected to column chromatography using 25 g of silica gel and a solvent of isopropanol:chloroform-concentrated aqueous ammonia = 4:1:1 by volume. The eluate is taken in 12 ml portions and fraction Nos. 30–50 are combined and concentrated to dryness under reduced pressure. As the result, 170 mg of the unreacted starting material is recovered.

Then, fraction Nos. 69–95 are concentrated under reduced pressure to obtain 147 mg of 3''-N-demethyl-1-N-(DL-α-hydroxy-β-aminopropionyl) XK-62-2 [i.e., Compound (II-1)].

Rf values of Compound (II-1) and the starting compound obtained from silica gel thin layer chromatography under the same conditions as in Example 1 are 0.37 and 0.48 respectively.

Melting point: 133°–140.5° C
Infrared absorption spectrum: $\sigma_c = 0\ 1640\ cm^{-1}$
Nuclear magnetic resonance spectrum (in $D_2O$, pD = 1.0)
δ (in p.p.m. from DSS): 1.29(3H, s), 2.78(3H, s), 5.19(1H, d, J = 4.0 Hz), 5.81(1H, d, J = 3.5 Hz)
Elementary analysis: Calculated for $C_{22}H_{44}N_6O_9 \cdot H_2O$: C = 47.64%; H = 8.36%; N = 15.15%. Found: C = 48.01%; H = 8.71%; N = 15.42%.

Fraction Nos. 97–131 are concentrated to dryness under reduced pressure to obtain 77 mg of 3''-N, 6'-N-didemethyl-1-N-(DL-α-hydroxy-β-aminopropionyl) XK-62-2 [i.e., Compound (I-1)].

Rf values of Compound (I-1) and the starting compound obtained from silica gel thin layer chromatography under the same conditions as in Example 1 are 0.29 and 0.48 respectively.

Melting point: 184.5°–195° C

Infrared absorption spectrum: $\nu_c = 0\ 1640\ cm^{-1}$

Nuclear magnetic resonance spectrum (in $D_2O$, pD = 0.9) δ (in p.p.m. from DSS): 1.28(3H, s), 5.18(1H, d, J = 3.8 Hz), 5.67(1H, d, J = 3.6 Hz)

Elementary analysis: Calculated for $C_{21}H_{42}N_6O_9 \cdot H_2O$: C = 46.83%; H = 7.86%; N = 15.60%. Found: C = 47.15%; H = 8.11%; N = 15.87%.

What is claimed is:

1. Compounds represented by the formula:

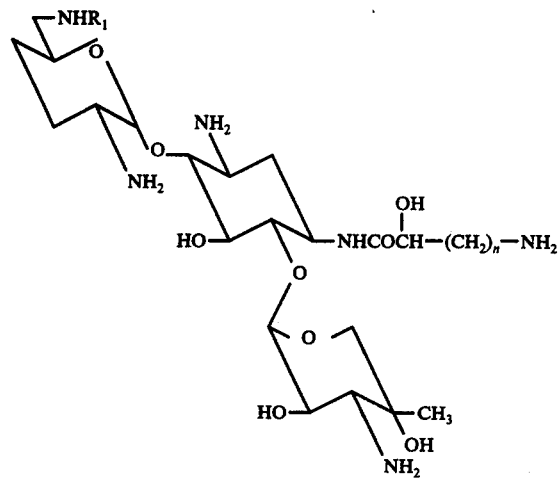

wherein $R_1$ represents a hydrogen atom or a methyl group, and $n$ is an integer of 1, 3 or 4, and the pharmaceutically acceptable, non-toxic, acid addition salts thereof.

2. The compounds of claim 1, wherein $R_1$ is a hydrogen atom and $n$ is 1.

3. The compounds of claim 1, wherein $R_1$ is a hydrogen atom and $n$ is 3.

4. The compounds of claim 1, wherein $R_1$ is a hydrogen atom and $n$ is 4.

5. The compounds of claim 1, wherein $R_1$ is a methyl group and $n$ is 1.

6. The compounds of claim 1, wherein $R_1$ is a methyl group and $n$ is 3.

7. The compounds of claim 1, wherein $R_1$ is a methyl group and $n$ is 4.

8. The sulfate salts of the compounds of claim 1.

* * * * *

UNITED STATES PATENT AND TRADEMARK OFFICE
CERTIFICATE OF CORRECTION

PATENT NO. : 4,097,664
DATED : June 27, 1978
INVENTOR(S) : SHINJI TOMIOKA, et al.

It is certified that error appears in the above-identified patent and that said Letters Patent are hereby corrected as shown below:

Col. 3, line 33 "6"-N" should be --6'-N--;

Col. 4, line 16 "1010°C" should be --100°C--;

Col. 6, line 41 "carbonyl" should be --carboxyl--;

Col. 13, line 37 "$[\alpha]_3^{29}$" should be --$[\alpha]_D^{29}$--;

Col. 16, line 56 "$\nu_\sigma$" should be --$\nu_C$--.

Signed and Sealed this

Second Day of January 1979

[SEAL]

Attest:

RUTH C. MASON
*Attesting Officer*

DONALD W. BANNER
*Commissioner of Patents and Trademarks*